United States Patent [19]

Glass et al.

[11] Patent Number: 5,306,414

[45] Date of Patent: Apr. 26, 1994

[54] CORROSION SENSOR

[75] Inventors: Robert S. Glass, Livermore; Willis L. Clarke, Jr., San Ramon; Dino R. Ciarlo, Livermore, all of Calif.

[73] Assignee: Regents of the University of California, Oakland, Calif.

[21] Appl. No.: 61,724

[22] Filed: May 17, 1993

[51] Int. Cl.$^5$ ............... G01N 17/02; G01N 27/27
[52] U.S. Cl. .................... 204/404; 204/412; 204/416; 204/433; 204/435
[58] Field of Search ............ 204/412, 404, 416, 433, 204/435

[56] References Cited

U.S. PATENT DOCUMENTS

| | | | |
|---|---|---|---|
| 4,568,445 | 2/1986 | Cates et al. | 204/412 |
| 4,752,360 | 6/1988 | Jasinski | 204/404 |
| 4,805,624 | 2/1989 | Yao et al. | 204/406 |
| 4,833,622 | 5/1989 | Barto et al. | 204/404 |
| 5,120,421 | 6/1992 | Glass et al. | 204/406 |

OTHER PUBLICATIONS

NADC-SIRLAB-1089, "Development of A Multiple Element Sensor For Localized Corrosion Of Stainless Steel", T. P. Anguish et al., 1989, pp. 562-572.
UCRL-JC-106690, "Preparation of Solid Membrane Chloride Ion-Selective Electrodes By Ion Implantation", R. S. Glass et al., Dated Feb. 1991.

*Primary Examiner*—John Niebling
*Assistant Examiner*—Kishor Mayekar
*Attorney, Agent, or Firm*—Henry P. Sartorio; Lafayette E. Carnahan

[57] ABSTRACT

A corrosion sensor array incorporating individual elements for measuring various elements and ions, such as chloride, sulfide, copper, hydrogen (pH), etc. and elements for evaluating the instantaneous corrosion properties of structural materials. The exact combination and number of elements measured or monitored would depend upon the environmental conditions and materials used which are subject to corrosive effects. Such a corrosion monitoring system embedded in or mounted on a structure exposed to the environment would serve as an early warning system for the onset of severe corrosion problems for the structure, thus providing a safety factor as well as economic factors. The sensor array is accessed to an electronics/computational system, which provides a means for data collection and analysis.

11 Claims, 6 Drawing Sheets

CORROSION SENSOR

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to detecting the onset of particularly severe corrosion problems and to sensing various elements and compounds in the environment, particularly to sensing environmental conditions which cause corrosion of materials, and more particularly to a corrosion sensor array and monitoring method capable of simultaneously sensing various environmental conditions which cause corrosion of materials and the associated instantaneous corrosion properties/response of structural materials of importance.

Virtually, every structural material in common use is affected by corrosion. For the U.S. economy, the loss of materials due to corrosion carries an annual price tag of tens of billions of dollars. Virtually, all structural materials corrode when placed in liquid or atmospheric environments, particularly in urban/industrial areas. The rates and modes of corrosive attack differ for different materials. Corrosion properties must always be evaluated when selecting materials for use in land vehicles, particularly public transportation, water-craft of all types, aircraft, bridges, buildings, etc. Beside the purely economic factors, there are the even more important issues of human safety which could be jeopardized when structures used for transport and housing are weakened by corrosion.

The rates/modes of corrosive attacks on a given material/metal are related to environmental conditions in which the material/metal is placed. These environmental conditions include such factors as pH and the presence of high concentrations of various ions, such as chloride, sulfide, etc. Therefore, it would be advantageous if a means was available for producing a corrosion sensor which could be embedded in, or emplaced on, various structures and provide an "early warning system" to guard against catastrophic failures of structural materials. Alternatively, such a device could find use in monitoring other environmental conditions, such as acid-rain. In the latter an application, the "detector" portion of the sensor system could be used in a disposable fashion.

Since corrosion is an electrochemical process, sensor systems based on electrochemical methods are well-suited for indicating particularly detrimental corrosive conditions. Various electrochemical sensors (electrodes) are known in the art, as exemplified by U.S. Pat. No. 5,120,421 issued Jun. 9, 1992 to R. S. Glass et al. and document UCRL-JC-106690, "Preparation of Solid Membrane Chloride Ion-Selective Electrodes by Ion Implantation", R. S. Glass et al., February 1991.

There has apparently been very little work directed to the development of corrosion sensors which can be used in-situ. A sensor based upon well-known principles of galvanic corrosion has been designed for atmospheric marine environments, see V. S. Agarwala, "Corrosion Monitoring of Shipboard Environments", ASTM Special Technical Publication 965, S. W. Dean and T. S. Lee, Eds., ASTM, 1986, p. 354–365. A single-element corrosion sensor functioning on the basis of electrical resistance has been designed, see S. T. Stropki et al., Proceedings of the 1989 Tri-service Conference on Corrosion, Report NADC-SIRLAB-1089, V. S. Agarwala, Ed., published by Defense Logistics Agency, Alexandria, Va., 1989, p. 544–561. The electrical resistance method of detection operates on the principle that the electrical resistance of a metallic conductor increases as the cross-sectional area decreases. Thus, one fabricates a device, or deposits a metal of a defined area and geometry and monitors resistance changes between two points. The resistance is related to cumulative corrosion of the metal. The probe can be made from a single material, such as aluminum alloy, 7075-T6. This electrical resistance type sensor was designed for emplacement in difficult to monitor locations on aircraft (helicopters) and proposed for cumulative corrosion monitoring.

A two-element corrosion sensor, consisting of an electrical resistance (ER) probe and an element for linear polarization resistance (LPR) measurement has also been designed, see F. Ansuini, NADC-SIRLAB-1089, p. 533–543. For this sensor, cumulative corrosion is measured by the ER element, while instantaneous measurements of corrosion rates are made using the LPR element. This sensor was proposed for both dry and wet environments, such as in dry and humid air.

A multiple-element sensor has been proposed for evaluating the localized corrosion of stainless steel in bleaching processes, see T. P. Anguish et al., "Development Of A Multiple Element Sensor For Localized Corrosion Of Stainless Steel", NADC-SIRLAB-1089, 1989, p. 562–572. This multiple-element sensor included an electrode of stainless steel, a coated Ag/AgCl reference electrode, a temperature transducer, a Ag/AgCl chloride sensor, and a pH electrode, and by monitoring these parameters the critical regions where pitting is probable can be avoided.

Multielement sensors have not been previously proposed for monitoring corrosion processes which utilize microelectrodes, which have analytical advantages, and which may be used in common sensor arrays.

While various corrosion sensors are known, as pointed above, there is a need for corrosion monitors which can be embedded in, or emplaced on, various structures, or which can be used in environmental monitoring stations, which enables simultaneous measurement and correlation of corrosion properties of structural materials and environmental conditions leading to corrosion. This can be accomplished by using a plurality of individual sensors with each sensor being constructed to detect a different corrosive component or composed of the structural material of interest. The present invention fills such a need by providing a monitoring method utilizing an array of electrodes (sensors), each individual sensor of the array being constructed for detecting elevated concentrations of a specific corrosion-causing ion, parameter, corrosion product, etc., such as measuring a chloride ion, sulfide ion, copper ion, pH, etc., whereby comprehensive and near-simultaneous measurement may be obtained by sequentially accessing the individual array elements. A number of such arrays would be embedded in or emplaced on a structure to be monitored or situated in various environments, and provide an indication of the real-time corrosion behavior of specific structural materials and the environmental factors which dictate the corrosion rates and mechanisms for these materials. Thus, the array of sensors are environmental/corrosion monitors. An inspector can obtain information from the sensors by using a hand-held instrument, or the sensors could be used without operator interface and be deployed in the field with periodic information being telemetrically relayed to a remote data processing facility. Periodic inspections or continuous monitoring are possible, with the preferred mode of operation being apparent from the application.

SUMMARY OF THE INVENTION

It is an object of the present invention to provide a corrosion sensor for in-situ monitoring.

It is a further object of the present invention to provide environmental/corrosion monitoring method using an array of electrochemical sensors for measuring different elements, ions, or parameters affecting a specific structure.

A further object of the invention is to provide a corrosion sensor array having individual sensors for simultaneously measuring concentrations of different chemical elements, ions, or parameters affecting or indicating the degree of environmental corrosivity.

Another object of the invention is to provide a corrosion monitoring system incorporating an array of different component electrochemical sensors from which is obtained multivariate data using a hand-held instrument or with the system deployed in field applications.

Another object of the invention is to provide a corrosion monitoring system incorporating an array of different component electrochemical sensors from which is obtained multivariate data in a field deployed system, or otherwise distributed over a structure, and the information obtained using a central electronics/computational panel, or telemetrically relayed to a remote data processing facility.

Another object of the invention is to provide an array of electrochemical micro-sensors which can be embedded in or emplaced on a structure to be monitored for environmentally-induced corrosion.

Another object of the invention is to improve the safety factor of a machine or structure by monitoring the structural materials thereof for corrosive effects caused by the environment.

Other objects and advantages of the invention will become apparent from the following description and accompanying drawings. Basically, the invention is a corrosion monitoring method using electrochemical sensors which can be embedded in or emplaced on various structures and provide an "early warning" system to guard against catastrophic failures, or to otherwise indicate changing, adverse environmental conditions (e.g. acid rain affecting corrosion). The invention involves an array of individual electrochemical sensors or electrodes, each constructed to detect or sense a specific chemical element or ion or other parameters of the environment in which the structural material being monitored, or environmental station, is located or used, with information from the individual sensors being obtained using a hand-held instrument, or accessed remotely with a central electronics/computational system, whereby corrosive effects of the environment on given structural materials can be evaluated. The sensor array may be fabricated by known deposition techniques or using a bundle of microelectrode wires as sensing elements. The invention provides a safety measuring factor with respect to the weakening of structural materials due to corrosion thereof, and is of particular value for transportation and structure safety, maintenance, and a determination of changing environmental conditions.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

The invention is a corrosion monitoring method and sensor array utilizing a plurality of individual electrochemical sensors or electrodes for measuring chemical species or ions present in the environment or other parameters of relevance to corrosion processes, which impact structural materials of importance located in a given environment. The information is obtained from the array of sensors by using a hand-held device or can be telemetrically relayed to a central data processing facility. Such information provides an "early warning" of potentially catastrophic corrosive effects on the structural material of interest. The array of sensors may be imbedded in or emplaced on the given structural material so as to provide in-situ corrosion/environmental monitoring of the structural material. Alternatively, the array can be used in remote environmental monitoring stations.

The present invention provides a safety factor as well as an economic factor, and has application for corrosion monitoring for transportation safety relative to bridges, tunnels, underpasses, overpasses, etc., as well as land vehicles, watercraft and aircraft maintenance. Also, the invention has applications for environmental monitoring, such as acid rain conditions and its effect on corrosion of structural materials, or other industrially or urban-induced problems. Thus, the invention is an in-situ corrosion/environmental monitoring system, using electrochemical sensors (electrodes) to provide information regarding environmental corrosivity.

Since the rates/modes of corrosive attack on a given metal/alloy are related to environmental conditions, such as low or high pH and the presence of a high concentration of chloride or other ions, and since corrosion is an electrochemical process, sensor systems based upon electrochemical methods are well-suited for indicating particularly detrimental conditions. They could, therefore, constitute an "early warning" alarm/monitor. Thus, the use of an array of electrochemical sensors (electrodes) which simultaneously monitor different chemical factors related to corrosion of chosen structural materials, and an embodiment of the material of interest, provide both maintenance and safety information.

Figure 1:
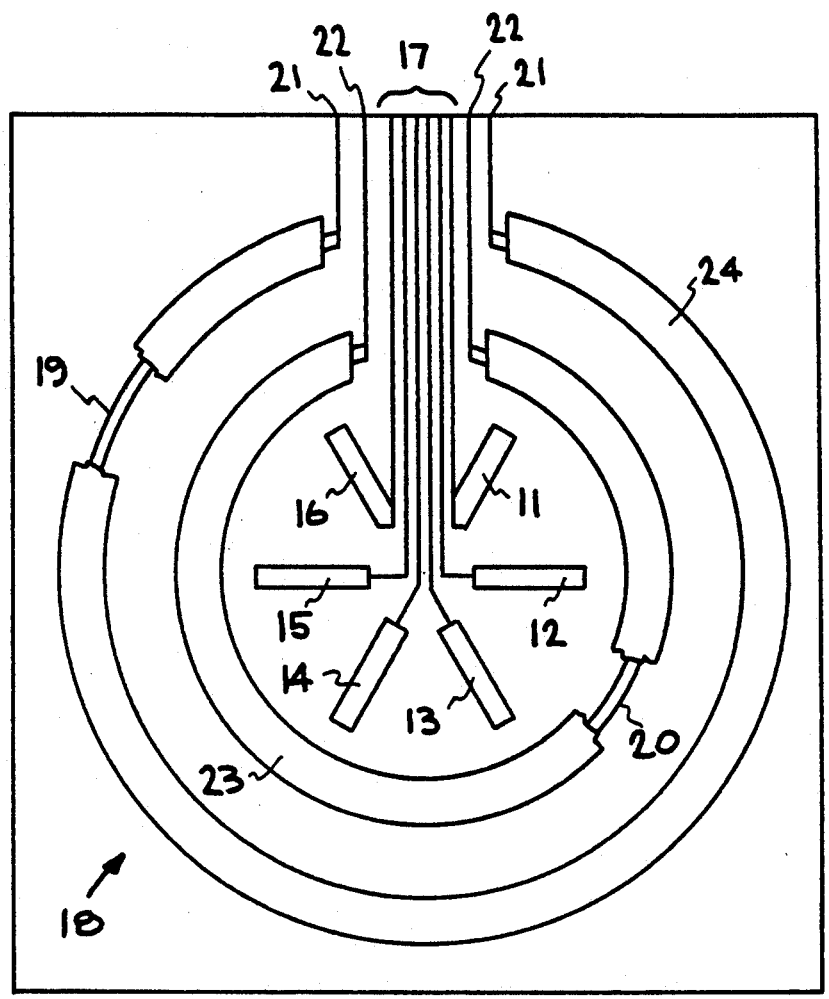
FIG. 1 illustrates an embodiment of an array of individual electrochemical sensors in accordance with the present invention.
Figure 2:
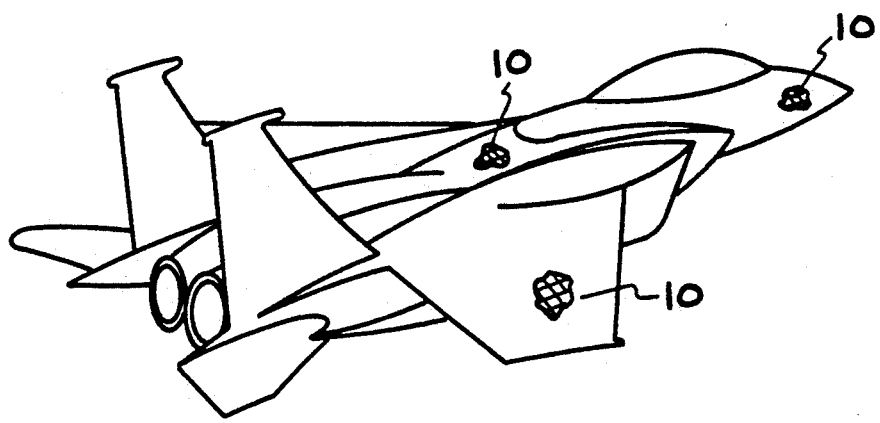
FIG. 2 illustrates an aircraft utilizing a plurality of the FIG. 1 sensor arrays embedded at different locations in the frame of the aircraft.

FIG. 1 illustrates an embodiment of an array of individual electrochemical sensors (electrodes), each individual sensor being constructed for measuring a specific element or parameter. In this embodiment, the array indicated at 10 includes six (6) individual sensors (electrodes) which comprise a chloride ion sensor 11, a sulfide ($S^{-2}$, $HS^-$) ion sensor 12, a pH sensor 13, a copper ion sensor 14, (or some other sensor for corrosion products) and corrosion potential rate sensors 15 and 16 for two materials which would be used in the structure being monitored. The exact combination and numbers of elements to be sensed would be different depending upon expected environmental conditions, materials used, and applications. For instance, if one were using the monitors of sensor array 10 for aircraft, as illustrated in FIG. 2, aluminum alloys, such as 2024 and 7075, would be used as the elements for the corrosion potential rate sensors 15 and 16, respectively. In addition, when using aluminum alloys it is important to monitor the pH provided by sensor 13, since aluminum shows an accelerated corrosion rate at pH values less than 2 and greater than 10. The sensor or element used to monitor pH could be composed of iridium oxide ($IrO_2$), or some other solid-state pH-sensitive material. Also, when aluminum alloys are used, monitoring for high concentrations of chloride ion in the environment is needed (since high chloride ion concentrations accelerate localized attack such as pitting and crevice corrosion), and the sensor 11 which is sensitive to this element is included, which could be composed of silver coated with silver chloride. In other environments, monitoring for sulfide is important since high concentrations of this ion can cause corrosion of alloys, particularly stress corrosion cracking. Finally, a sensor which detects corrosion products from an alloy, such as copper ion, would indicate the extent of corrosion. The materials out of which one could fabricate a sulfide ion sensor (12) or a copper ion sensor (14) include silver sulfide (AgS) and a mix of copper sulfide (CuS) and $Ag_2S$, respectively. The preferred diameter of the sensor electrode is 10-50 $\mu$m.

The sensors 11-16 of array 10 are located within a ring-like assembly generally indicated at 18 and composed for example of an outer ring 19 and an inner ring 20 connected to respective electrical leads 21 and 22. The electrical lead lines are extended up to contat pads, to interface with measurement circuitry. The distance from the contact pads to the outer ring 24 is variable, but commonly 2 mm-1 cm. Each of rings 19 and 20 have a coating layer 23 and 24, respectively thereon which may be a polymer or other material, for masking purposes. The inner ring 20 is termed the reference electrode, and may be composed of Pt, Ag, or Ag coated with a layer of AgCl, or any of these materials coated with a polymer layer containing known concentrations of ions. The material of ring 20 must provide a stable potential. This is accomplished by using a chemically-poised system, that is, in equilibrium with constant activities of the relevant ions/materials. The choice of ring 20 composition will depend upon environmental conditions and application. The choice/nature of the reference electrode will be understood by those skilled in the art. One preferred embodiment of inner ring 20 is Ag or Ag coated with a layer of AgCl and then coated with a polymer layer or ionomer, such as Nafion, a Trademark of Dupont, to keep the concentration of chloride ion constant. The preferred width of the reference electrode (inner ring 20) is 20 $\mu$m and the thickness thereof is 0.2 $\mu$m, although this is variable.

The outer ring or counter electrode 19, may or may not be used. Its use would depend upon the measurement strategy. The use of this electrode (ring 19) would be understood by those skilled in the art. When it is included in the array, the preferred material for its construction is PT. The preferred width of the counter electrode (outer ring 19) is 20-50 $\mu$m with a thickness of 0.2 $\mu$m, although this is variable.

The dimensions and relative spacings between the sensor elements or electrodes 11-16 and between the sensor elements and the inner ring (reference electrode) 20 is dependent upon the exact application. The preferred dimensions (diameters) of the sensor elements is 10-50 $\mu$m and thickness of 2 $\mu$m. The reference electrode (inner ring) should be placed in proximity to the sensor elements, preferably less than 30 $\mu$m. The width of the counter electrode as set forth above is preferably 20-50 $\mu$m and its thickness is 2 $\mu$m. The spacing of the counter electrode (outer ring 19) with respect to the sensor elements 11-16 is variable. A spacing of about 1.5-2 mm between the counter electrode and the sensor electrodes (11-16) is generally sufficient (and in some cases much more than necessary). The correct spacing is dependent upon diffusional processes and the experimental method, as understood by those skilled in this art. Different spacings and geometric designs for the sensor arrays are possible.

The sensor, reference, and counter electrodes are deposited onto an inert substrate, such as alumina or insulated silicon. E-beam evaporation or dc magnetron sputtering are two common deposition techniques. The fabrication sequence is set forth hereinafter.

Figure 7:
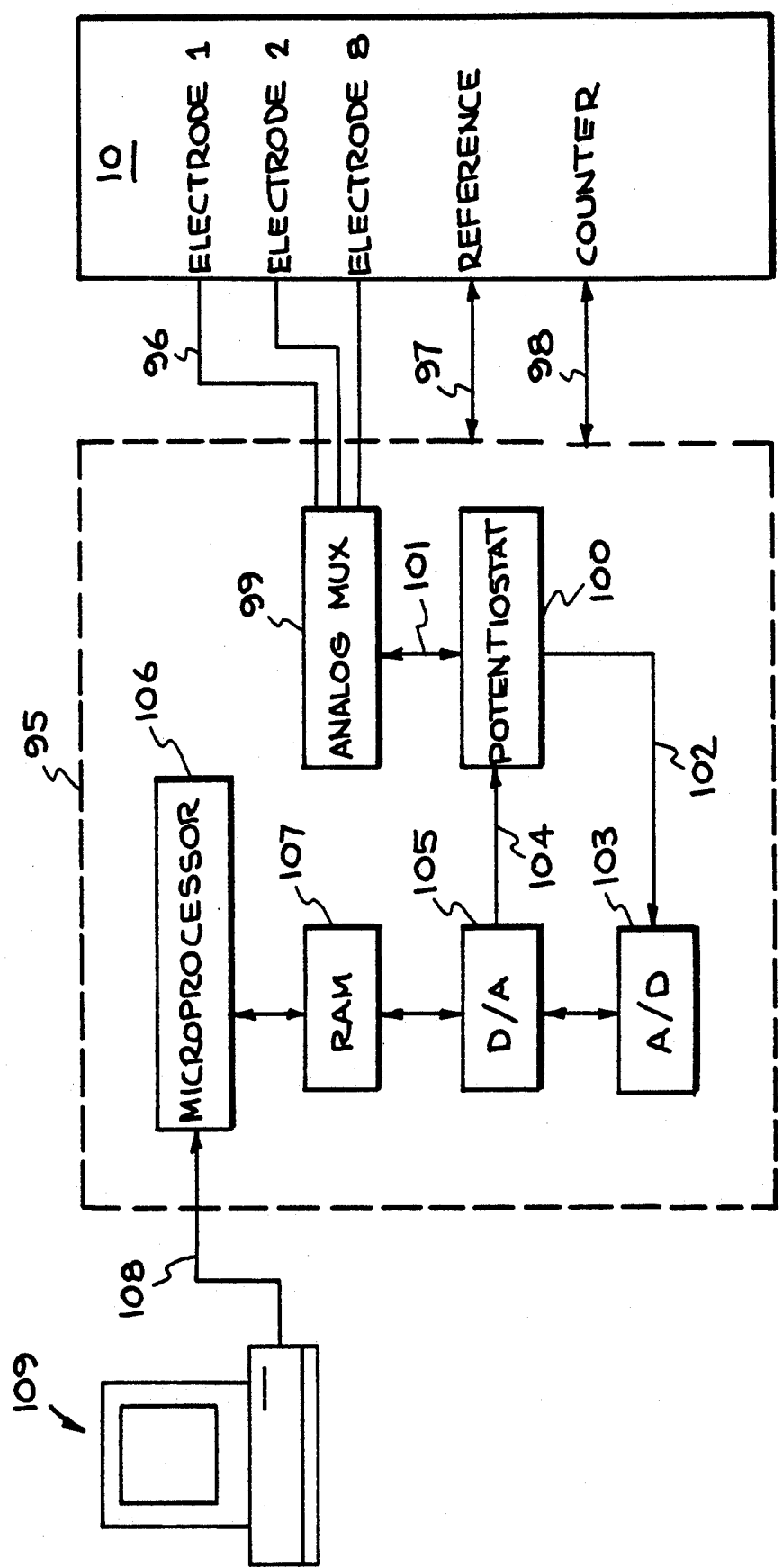
FIG. 7 illustrates in block diagram form one in-use arrangement for the sensors, electronic hardware, and computational facilities, used with a sensor array such as the eight (8) electrode embodiment of FIG. 3.

As shown in FIG. 2, sensor arrays 10 are embedded in the aircraft at selected locations, and while only three arrays 10 are illustrated, a large number of such arrays may be used to monitor the various major components of the aircraft. As seen in FIG. 1, each of the sensors 11-16 is provided with a signal output, generally indicated at 17 by which information from the various sensors may be transmitted to a central electronics/computational system, such as shown in FIG. 7, but may be similar to the read-out system of above-referenced U.S. Pat. No. 5,120,421. The central system may be located, for example, at a panel in the cockpit in the aircraft of FIG. 2, or the signals from the various arrays may be collected on the aircraft by hand-held instrumentation, and later transmitted to a maintenance base for the aircraft. Within the aircraft, the signals from the sensors could be transmitted electrically (through conventional wires) or using electromagnetic radiation. Alternatively individual arrays may have electrical connections protruding to the nearest surface of the aircraft structure, such that these sensors could be read by maintenance inspectors using a hand-held instrument.

It is to be noted that only the sensor elements or electrodes, such as elements 11-16 in FIG. 1, the reference electrode (inner ring) 20, and the counter electrode (outer ring 19) are exposed to the environment. All other metallic surfaces, lead lines, electrical contact pads, etc. are masked by a non-porous, non-conductive layer of material such as silicon nitride, polyimide, silicon dioxide, etc. The thickness of the layer is commonly 1-5 μm.

The type and number of sensors in each array is dependent on the number of structural materials of interest and the environment. For example, if the arrays were used to monitor corrosion in underground pipes or bridges, copper or steels would be used for the corrosion potential sensors 15 and 16 of FIG. 1, and the type of sensors 11-14 used would depend on the local environment. In any case, the arrays are used to monitor several environmental factors, most importantly, the instantaneous corrosion behavior of specific structural materials and the environmental factors which dictate the corrosion rates and mechanisms for those materials. In this sense, the sensors are environmental/corrosion monitors.

Figure 3:
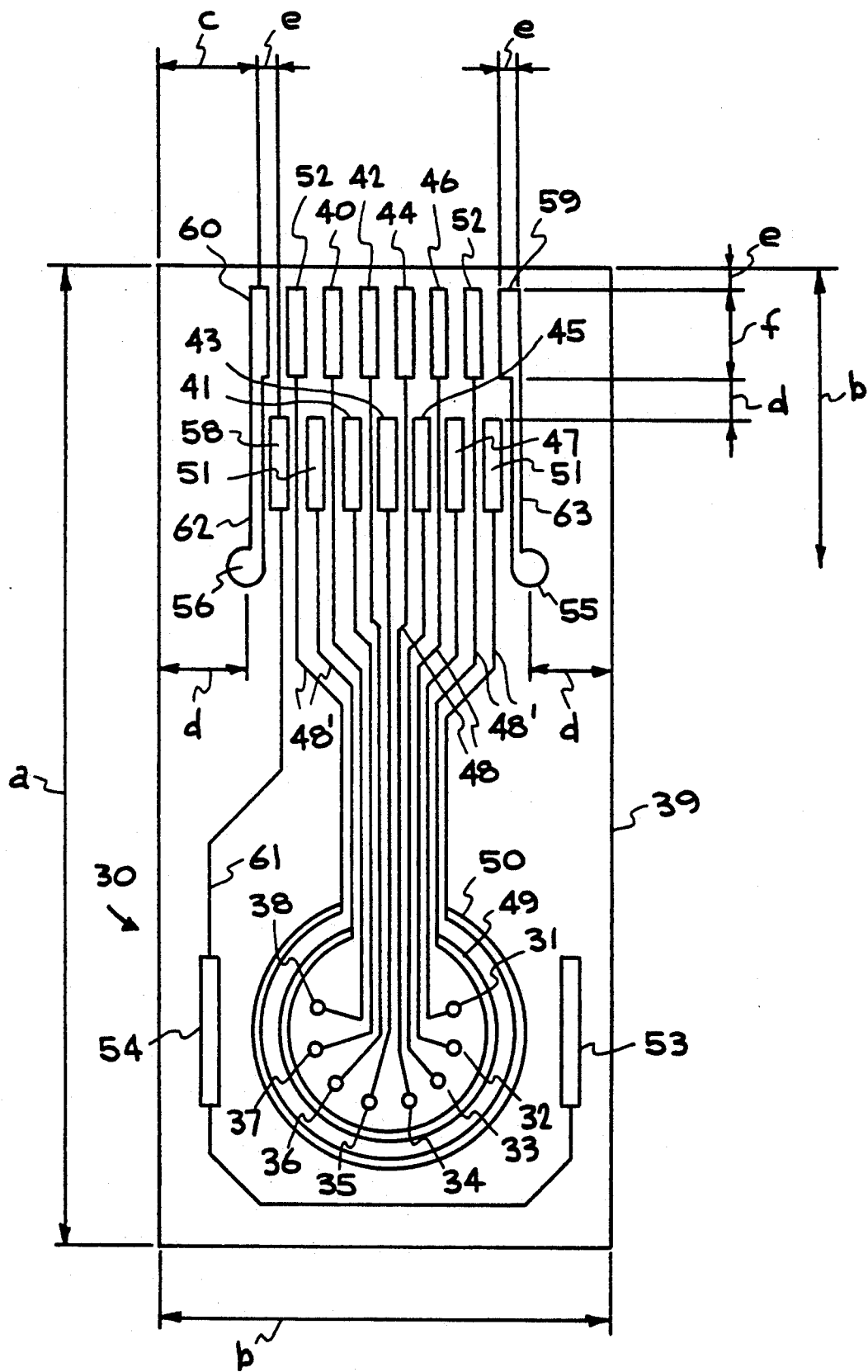
FIGS. 3 and 4 illustrate other embodiments of the sensor array made in accordance with the invention.

FIG. 3 illustrates another embodiment of the sensor array using eight (8) sensor elements. An array 30 of eight (8) individual electrochemical sensors (elements) 31-38 is mounted on a substrate 39.

The sensors 31-38 are each connected to a respective signal output contact pad 40 via lead lines 48, and are located within an inner ring or reference electrode 49 which is located within an outer ring or counter electrode 50, as in the FIG. 1 embodiments. Each of electrodes 49 and 50 are connected to a pair of contact pads 51 and 52, respectively via lead lines 48'. The parameters, materials, etc. of the sensors 31-38 may be the same as described above with respect to the FIG. 1 embodiment, or composed of different materials, depending on the specific application using an eight (8) sensor array instead of a six (6) sensor array, with the two additional sensors constructed to evaluate different, and additional, environmental factors and materials.

The eight element sensor of FIG. 3 is provided with two pair of test electrodes indicated at 53-54 and 55-56, with electrodes 53-54 being connected via a lead 57 and electrodes 54, 55, and 56 being connected to contact pads 58, 59 and 60 via respective electrical leads 61, 62 and 63. The test electrodes 53 and 54 are located on opposite sides of sensors 31-38, with test electrodes 55 and 56 being positioned in spaced relation adjacent the contact pads for sensors 31-38. The test electrodes are connected to a power supply, not shown.

There are two functions for the test electrodes. The electrodes 53 and 54 are used to test for pinholes in the polyimide or photoresist coatings, and the test electrodes 55 and 56 are used for electronic calibration. In order to test for pinholes, the array is immersed in a conductive solution, say 1 molan NaCl, until the sensor electrodes, reference counter electrode assembly, and the test electrodes 53 and 54 are covered with the solution. A voltage (typically 2-3 V) is applied between the test electrodes 53 and 54 and the reference electrode, 49. Since the test electrodes are covered by a polyimide layer or other coating, no current should flow due to electrolysis, unless pinholes in this coating are present.

The other test electrodes, 55 and 56, are used for calibration of electronic measurement equipment used to obtain information from the sensors. For example, a standard resistor may be attached between these leads and various waveforms applied for test.

For purpose of illustration of the test array arrangement of FIG. 3, various parameters are identified as a, b, c, d, e, and f wherein: a=3.81 cm, b=1.27 cm, c=0.19 cm, d=0.13 cm, e=0.06 cm, and f=0.38 cm, with the diameter of electrodes 55 and 56 being 0.15 cm.

Figure 4:
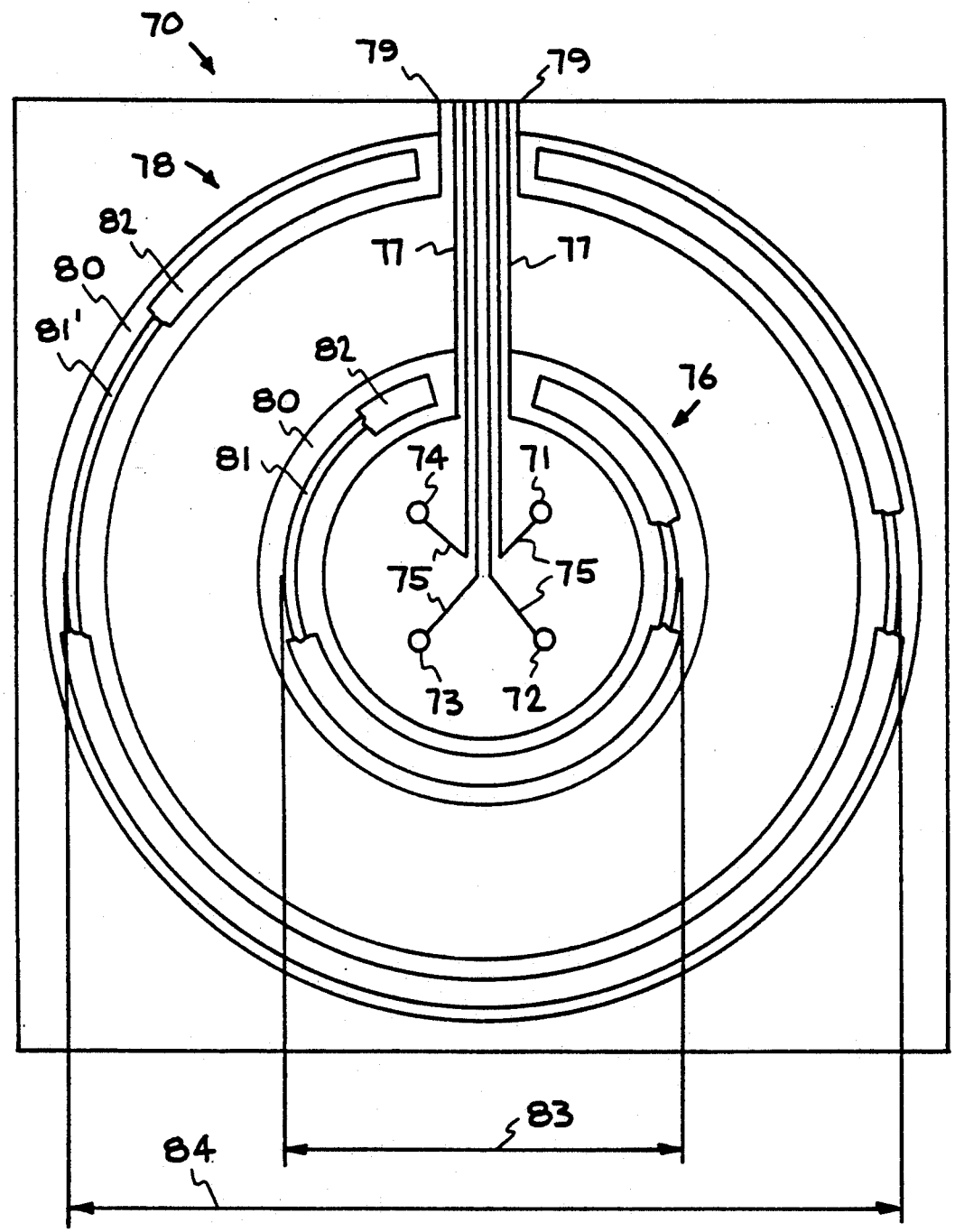

FIG. 4 illustrates an embodiment of the invention using a four (4) sensor array, with each of the individual sensors or electrodes being constructed for measuring a specific element, ion, or parameter. In this embodiment, the array indicated at 70 includes four individual sensors (electrodes) 71, 72, 73 and 74, which may be constructed to be sensitive to chloride ions, sulfide ions, copper ions, pH, or measure the corrosion potential/rate of a specified material of interest, etc., as described above. Each of the sensors 71-74 are provided with a signal output lead 75. The sensors 71-74 are located within an inner ring or reference electrode generally indicated at 76 having signal leads 77, and the inner ring 76 is located within an outer ring or counter electrode 78 having signal leads 79. The inner (reference) and outer (counter) rings or electrodes are each constructed of a base layer 80, such as gold, a reference electrode layer 81, such as silver, or silver coated with silver chloride, and a counter electrode layer 81; which are partially covered with a coating 82 of a polymer or other appropriate material, such that only a central portion of layers 81 and 81' is exposed. In all cases, the underlying base layer 80 is either covered by the reference or counter electrode material, or polyimide.

By way of example only, the diameter of ring or reference electrode 76, as indicated at 83 is 2.4 mm and the diameter of outer ring or counter electrode 78, as indicated at 84 is 5.6 mm. The width of layer 80 may be 200 to 300 μm with a thickness of 0.5 μm, the width of layers 81 and 81' may be 100 to 150 μm and thickness of 0.1 to 0.2 μm with 10 to 50 μm being exposed, and the remainder covered by coating or layer 82 having a thickness of 1 to 5 μm and composed of material such as silicon dioxide, silicon nitride, or polyimide.

Figure 5:
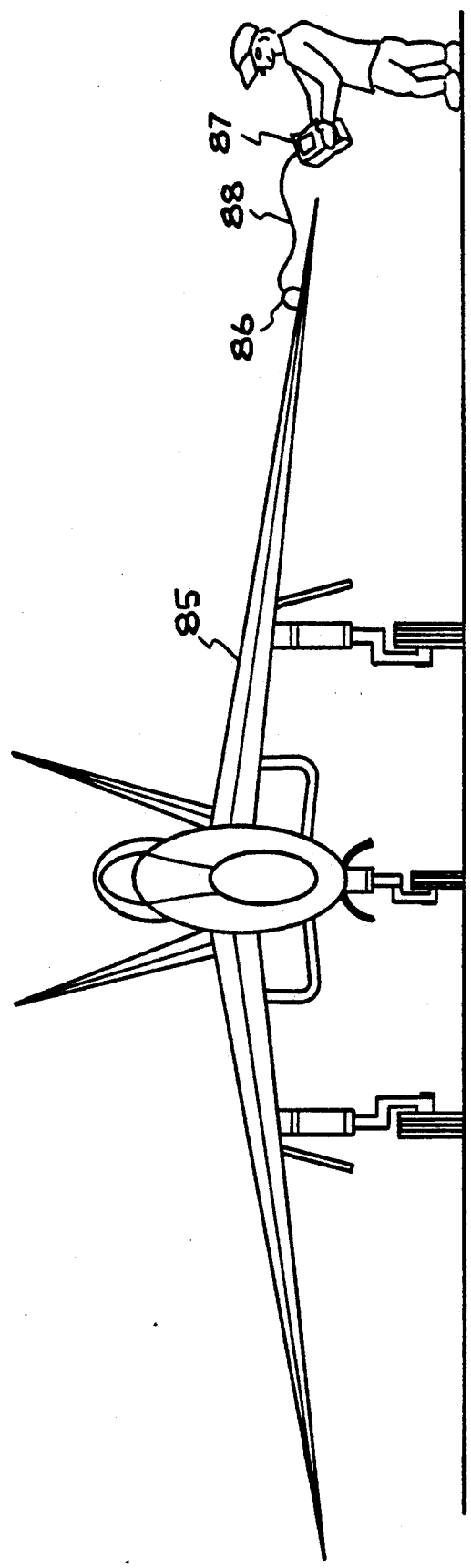
FIG. 5 illustrates the use of the sensor array in conjunction with a hand-held instrument for obtaining information.

FIG. 5 illustrates a hand-held readout means for detectors mounted on an aircraft, such as shown in FIG. 2. Here, the aircraft 85 is provided with a junction point 86 to which leads from the various arrays 10 of electrochemical sensors are connected. A hand-held readout device 87 is connected via cable 88 to junction point 86, whereby a readout from each of the arrays 10 located on various sections of the aircraft can be obtained.

The readout device, 87, surveys the individual sensor arrays 10 to provide extended area corrosion information. The individual sensor, on each array, (e.g. 1-16 of FIG. 1, or 71-74 of FIG. 4) are accessed in any order. Standard potentiometric or viltammetric methods, as described in several textbooks (see, for example, A. J. Bard and L. R. Faulkner, Electrochemical Methods Fundamentals and Applications, John Wiley and Sons, New York, 1980) or corrosion rate measurements such as linear polarization resistance or Tafel extrapulation (see, for example, M. G. Fontana and N. D. Greene, Corrosion Engineering, McGraw-Hill, San Francisco, 1978), are used to obtain environmental/corrosion information from the elements/arrays. The specific technique used for any particular element of any array will be understood by those skilled in the art.

In the particular example embodiment shown in FIG. 5, the readout device could provide instantaneous visual information to the operator, or it could store information for transmittal to a more sophisticated host computer for analysis. The circuitry used for making the measurements is described below, and is also explained in U.S. Pat. No. 5,120,421, and by other high input impedance voltmeter instruments.

Figure 6:
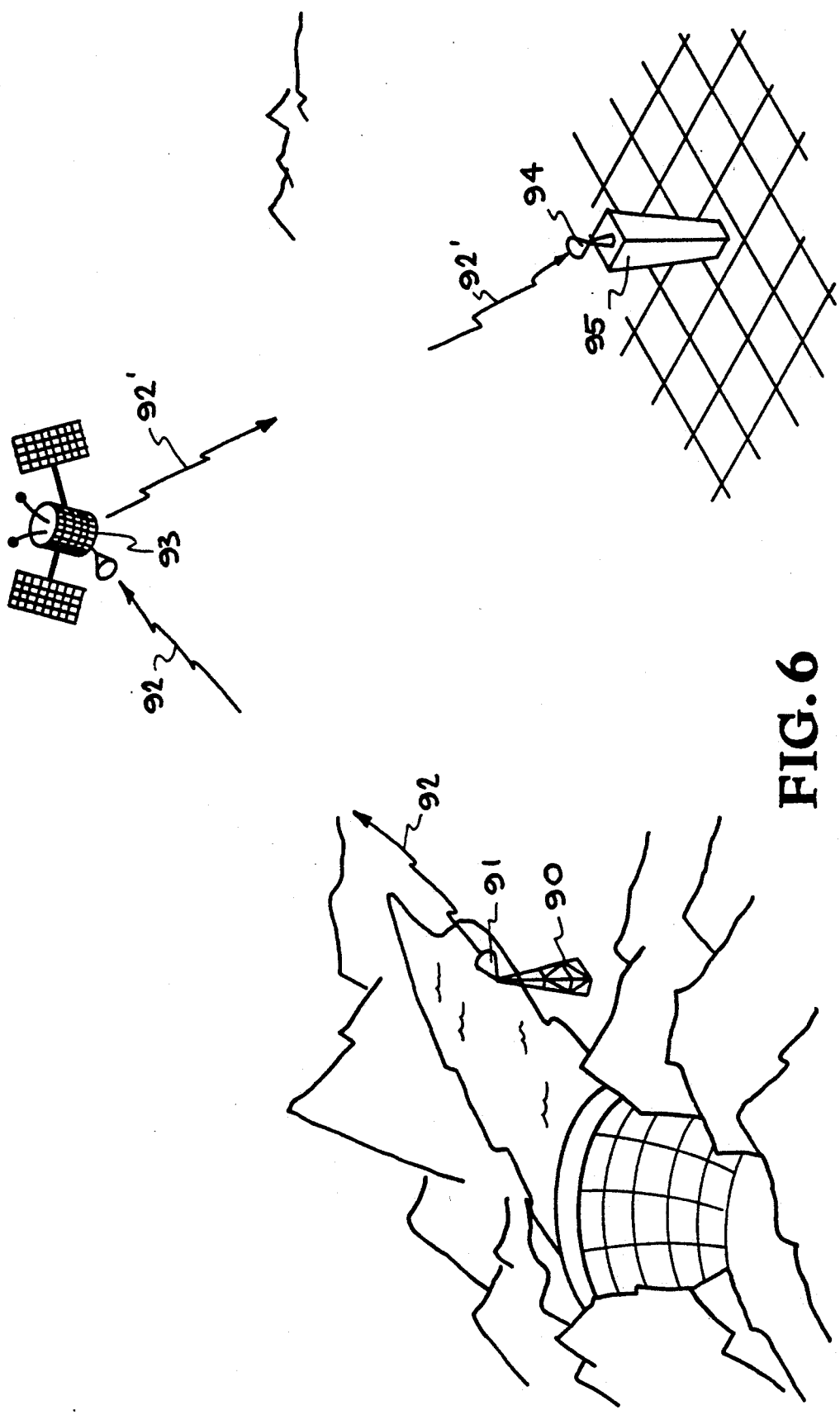
FIG. 6 illustrates the use of the sensor array contained within an environmental monitoring station, and information being telemetrically relayed to a central data processing facility.

FIG. 6 represents an embodiment of a system for the "monitoring" stations equipped with the sensor arrays of this invention, and which are exposed to prevailing conditions. In this arrangement, the sensor elements can be used to monitor environmental conditions, such as acid rain, and the potential effect thereof on structural materials used in these environments. As illustrated in FIG. 6, the system basically comprises a monitoring station 90 on which is mounted a signal transmission mechanism, illustrated by dish 91 which transmits signals 92 to a satellite 93, which in turn transmits the signal 92' to a signal receiving mechanism illustrated by dish 94 operatively connected to a data processing facility 95.

FIG. 7 represents, in block diagram, the electronic circuitry and analysis system components used with the arrays. The system shown would comprise a hand-held or portable unit, and would also be part of the remote system using telemetry shown in FIG. 6. The analog multiplexor, 99, selects the appropriate sensor electrodes of the sensor array 10 over lines 96. The multiplexor communicates over lines 10, with the potentiostate, 100. It is the potentiostat which enforces potentials to the reference electrode and forces currents through the counter electrode/sensor electrode pair (control channels 97 and 98). Commands to the potentiostat, and data back out, are handled by the digital-to-analog and analog-to-digital converters, 105 and 103, respectively, which communicate with the potentiostat over lines 104 and 102, respectively. The random access memory, 107, stores information. A built-in microprocessor, 106, is used to down-load information and waveforms from a host computer 109. To accomplish this, a RS232 serial line 108 is used. The system 95 comprises the hand-held circuitry. In reference to FIG. 6, the information control line 108 could also include telemetry.

At least two different methods can be used to fabricate the arrays. The first of these methods is photolithography with negative lift-off, or some other masking procedure, coupled with electron-beam or magnetically-assisted sputter deposition of the individual sensor materials. Sequential deposition of different electrode materials permits the fabrication of multielement arrays. Generally, following deposition the as-deposited sensor elements will be chemically or physically modified in order to enhance chemical selectivity. For instance, to fabricate an electrode sensitive to chloride ions, $^{35}Cl^+$ can be ion-implanted into a silver substrate, see above-referenced UCRL-JC-106690. Similarly, in order to create a solid-state pH microelectrode, oxygen may be ion implanted into an iridium substrate. Alternately, an as-deposited iridium or silver substrate may be electrochemically oxidized in specific electrolytes by known techniques in order to create iridium oxide or silver chloride surfaces, respectively.

By way of example, an array as illustrated in FIG. 1 and using the types of sensors 11-14 described above with respect to FIG. 1 with aluminum alloys 2024 and 7075 as the material for sensor 15 and 16, and with the external ring-like assembly 18 being composed of rings 19 and 20 of platinum and silver, would be fabricated using a photolithography/sputter deposition method. The arrays may be fabricated using a procedure similar to that set forth in above referenced U.S. Pat. No. 5,120,421.

A slightly different process is outlined below, wherein 5.08 cm diameter silicon wafers, 1 mm thick, are used as substrates, and a combination of 5000 Å of thermal oxide plus 2000 Å of silicon nitride is used to electrically isolate the sensor films from the silicon substrate. Two sensors can be fabricated on each substrate or wafer, and when completed the sensors can be cut to a final size (1.27 cm by 3.81 cm) with a dicing saw. An all lift-off procedure is used, wherein openings are patterned in the photoresist layer, the sensor material is then evaporated onto the entire wafer, and the unwanted material is lifted off by dissolving the resist in acetone. This eliminates the need for any chemical etching. After the sensor materials are defined in this manner, a photo-sensitive layer of polyimide is applied to the wafer and patterned with the openings required for the sensor electrodes and the connector pad area. The typical circular area of the exposed working electrode has a diameter of $50\mu$.

The following sets forth the fabrication process used in verification of the invention:

Silicon wafers, 1 mm thick (~40 -mils), 5.08 cm diameter were used as substrates for this sensor, because they are strong and not easily broken. Also, equipment is readily available to handle them. Commercial connectors are available to interface the support electronics with this substrates thickness. The wafers were insulated with an oxide/nitride dielectric to keep electrodes isolated. A 0.2 $\mu$m silicon nitride film on top of a $0.5\mu$ thermal oxide was used as the electrical insulator. Other candidates for substrates would be glass and ceramic.

In a lift-off process, photoresist is first patterned on the substrate so that the sensor metal can be subsequently evaporated everywhere and then lifted off where it is not wanted. Photomasks for the lithography were designed on a CALMA computer aided design (CAD) system. Contact printing in a mask aligner was used to define the patterns. A positive acting resist was used, which means that the resist which is exposed to UV light will develop away. The photoresist process for sensor metal difinition is described as follows:

Spin AZ1350J (made by Hoechst Celanese Corporation, Sumerville, N.J.) resist @3000 rpm.
Softbake @90° C. for 5 minutes.
Soak in chlorobenzene for 3 minutes. (This produces a lip to aid lift-off).
Let sample air dry.
Expose sensor metal pattern to UV irradiation for 17 sec. (570 mJ/cm$^2$).
Develop in 1:1 AZ 135 OJ (made by Hoechst) developer for 1 minute.
No hardbake so that resist will lift off.

The vacuum system used could hold six 5.08 cm wafers at a time for metal evaporation. With two sensors per wafer, 12 sensors can be simultaneously fabricated. 100 Å of titanium was used under the sensor metal for adhesion. Thickness of the sensor metal was 2000 Å. The active area of the sensor was defined by the final polyimide coating. A 50 $\mu$m diameter circular sensor area is typical. The sensor metal was used as the conductive lead from the sensor area up to the connector contact which was about 3.81 cm away, so that the sensor metal did not have to interface with another conductor. Care has to be taken with the power levels and heat generated during the metal evaporation to make certain that the resist does not overheat and crack. After vacuum deposition of sensor metal, the unwanted metal was lifted off by dissolving the patterned resist in acetone. The resist for the next sensor metal was then applied using the same process listed above. Alignment targets were used to properly align each sensor metal pattern.

Sensor materials include platinum, silver, gold, iridium and iridium oxide. All were evaporated in an e-beam evaporator with the exception of the iridium oxide. The iridium oxide was magnetron sputtered and the pattern was defined by using a molybdenum stencil mask.

The final step in the device fabrication was to cover everything with a film of polyimide, except for the actual sensor areas, the reference electrode, the counter electrode, some test pads, and the contact-pad area. We used the Ceba-Geigy photosensitive polyimide No. 348 made by OCG Microelectronics Materials, Inc. This is a negative acting photosensitive, that is it will not develop away if it is exposed with UV radiation. The polyimide process is as follows:

Spin on adhesion promoter @3000 rpm.
Spin on Probimide 348 @3000 rpm. (yields 5 $\mu$m thick coating when cured).
Softbake @90° C. for 20 minutes.
Expose mask with 600 mJ/cm$^2$ of UV energy.
Develop for 90 seconds in QZ3301, made by OCG Microelectronics, Inc., West Patterson, N.J.
Rinse for 20 seconds in 1:1 QZ3301:QZ3312 (made by OCG Microelectronics, Inc.
Rinse for 10 seconds in QZ3312.
Cure in a nitrogen atmosphere:
  1 hour @90° C.
  1 hour @120° C.
  3 hours @350° C.
  Cool slowly.

Sensors were cut to their final size with a dicing saw. Final size was approximately 1.27–3.81 cm. Conductive pads were designed at one end of the sensor so that a commercial electrical connector could be used to interface to data collecting electronics.

An alternative method for fabricating the arrays is to bundle together an array of microwires, exposing only the ends to the environment to be monitored. Microwires with diameters of 25 $\mu$m or less are commercially available from several sources.

In any case, microelectrode sensing elements are employed because they do not suffer from uncompensated resistance effects; they only require small volumes of solution (microliters, or even a moisture film); large signal-to-noise ratios are obtained; and the obvious advantage that because they are so small, they may be easily and inconspicuously emplaced on, or embedded in various structures. Above-referenced U.S. Pat. No. 5,120,421 exemplified an electrochemical sensor system utilizing a microelectrode array and describes a process for fabricating the array. Thus, where the microelectrode sensing elements are used as sensors 11–16 for the array 10 of FIG. 1, the sensors for the specific elements of FIG. 1 would be formed using the technique set forth U.S. Pat. No. 5,120,421 or variations herein described.

For any given structure several sensors, perhaps hundreds or thousands for large structures, would be imbedded in or emplaced on various parts of the structure, thereby insuring wide-coverage monitoring. During routine probing of the "state-of-the-structure", the individual sensors would be sequentially accessed and the information networked to a central electronics/computational system, whereby a complete review of the "state-of-corrosion" of the structure can be made. Alternatively, the various sensors could be "read" with a hand held device, and the data logged for later readout and evaluation.

It is to be noted that there are several factors to be considered for the use of the sensor devices. First, water, containing corrosive ions, must contact the sensor elements and the reference electrode, as well as the counter electrode if that element is used. Thus, a moisture film must exist. This will be possible in high humidity environments (>70% RH) and, of course, when the residence position of the sensor is flooded. There are ways of increasing the moisture content at the sensor surface, for instance, by applying hydrophilic coatings, such as hydrogels, polyethylene oxide or films grafted with hydrophilic monomers, such as acrylic acid, to the sensor array, or by embedding the sensors in a matrix which is intrisically hydrophillic. In any case, there must be ionic conductivity between the sensor and reference and/or sensor and counter electrodes. Of course, in the absence of appreciable water, corrosion is a slow process.

Another consideration is the spacing of the elements on the sensor array. For maximum performance, the sensor electrodes should be spaced closely to the reference electrode, less than 1 mm and preferably much closer.

Another consideration is calibration, the extent of which will have to be determined on an individual application basis. Temperature correction will often have to be done, and a temperature measuring device such as a resistance-temperature detector (RTD), which typically would be a platinum thin film or line of any dimension, could be incorporated as part of the array, or used externally. "Relative" measurements indicating changing conditions are easier to conceptualize. Quantitative measurements, for instance of the exact activity of chloride ions, are more difficult to arrive at. One way this could be accomplished is by incorporating, as an element of the array, a reference element wherein a known activity of chloride ions could be constrained within a polymer layer.

Another consideration is one of longevity. This again is a function of environmental conditions. It also is a function of sensor electrode area and thickness. Different designs could be used to handle various situations. For use in the embodiment shown in FIG. 6, and possibly FIG. 2, for example, the sensors could be replaced periodically. Disposable use could also be employed. More rugged sensors would be used in inaccessible application areas.

It has thus been shown that the present invention provides a means for assessing the structural integrity (environmental compatability) and thus the safety factor of bridges, ships, aircraft, vehicles, etc. The sensor array of this invention may be configured to detect changes in activities of deleterious (with regard to corrosion) ions in the environment and also to measure instantaneous corrosion properties of structural materials. Thus, it has wide application for a variety of materials and environmental conditions.

While particular embodiments of the sensor array have been illustrated and described, and specific fabrication techniques have been described, such is not intended to limit the scope of this invention. Modifications and changes will become apparent to those skilled in the art, and it is intended that the scope of this invention be limited only by the appended claims.

We claim:

1. An electrochemical corrosion sensor assembly providing in-situ corrosion/environmental monitoring and adapted to be embedded in or emplaced on a structure to be monitored, comprising:
- a sensor array;
- said sensor array including a plurality of individual sensors;
- certain of said plurality of individual sensors being constructed to be sensitive to chemical ions and factors present in a environment;
- certain of said plurality of individual sensors being constructed from a material which is the same as a metal or metal alloy structural material to be monitored, so that its corrosion potential/rate may be measured; and
- means operatively connected to each of said individual sensors for generating a signal and directing the signal therefrom to a point of use.

2. The electrochemical corrosion sensor assembly of claim 1, wherein said sensor array includes at least one ring-like member extending around said plurality of individual sensors, and having means operatively connected thereto for providing an electrically connection.

3. The electrochemical corrosion sensor assembly of claim 2, wherein said ring-like member is constructed from material selected from the group consisting of platinum, silver, and silver/silver chloride.

4. The electrochemical corrosion sensor assembly of claim 3, additionally including polymer coatings applied to at least the ring-like member to maintain constant ion activities and stable potentials.

5. The electrochemical corrosion sensor assembly of claim 2, wherein said ring-like member is composed of a plurality of rings, an inner of said rings functioning as a reference electrode, and an outer of said rings functioning as a counter electrode, said rings being constructed from material selected from the group consisting of platinum, silver, and silver/silver chloride.

6. The electrochemical corrosion sensor assembly of claim 1, wherein said plurality of individual sensors sensitive to environmental conditions are constructed to be sensitive to an environment element selected from the group consisting of chloride ions, sulfide ions, copper ions, and pH.

7. The electrochemical corrosion sensor assembly of claim 1, wherein said metals alloys are selected from the group consisting of aluminum, copper, iron, nickel and alloys thereof.

8. The electrochemical corrosion sensor assembly of claim 1, wherein said means includes a hand held readout mechanism.

9. The electrochemical corrosion sensor assembly of claim 1, wherein said means includes a data processing facility.

10. The electrochemical corrosion sensor assembly of claim 9 wherein said data processing facility is connected to said sensor array via a telemetric relay system.

11. The electrochemical corrosion sensor assembly of claim 1, wherein said individual sensors are constructed from material selected from the group of platinum, silver, gold, iridium, and iridium oxide.

* * * * *